United States Patent
Taarning et al.

(10) Patent No.: US 9,796,649 B2
(45) Date of Patent: Oct. 24, 2017

(54) PROCESS FOR REMOVING FORMALDEHYDE FROM A COMPOSITION COMPRISING GLYCOLALDEHYDE

(71) Applicant: Haldor Topsøe A/S, Kgs. Lyngby (DK)

(72) Inventors: Esben Taarning, Frederiksberg (DK); Martin Spangsberg Holm, Oxford (GB)

(73) Assignee: Haldor Topsoe A/S, Lyngby (DK)

( * ) Notice: Subject to any disclaimer, the term of this patent is extended or adjusted under 35 U.S.C. 154(b) by 162 days.

(21) Appl. No.: 14/769,161

(22) PCT Filed: Feb. 25, 2014

(86) PCT No.: PCT/EP2014/053587
§ 371 (c)(1),
(2) Date: Aug. 20, 2015

(87) PCT Pub. No.: WO2014/131743
PCT Pub. Date: Sep. 4, 2014

(65) Prior Publication Data
US 2016/0002137 A1    Jan. 7, 2016

(30) Foreign Application Priority Data

Feb. 27, 2013 (WO) ............... PCT/EP2013/053962
Nov. 18, 2013 (DK) ............................ 2013 70694

(51) Int. Cl.
| | |
|---|---|
| *C07C 45/86* | (2006.01) |
| *C07C 67/42* | (2006.01) |
| *C07C 29/14* | (2006.01) |
| *C07C 45/85* | (2006.01) |
| *C07C 29/143* | (2006.01) |
| *C07C 209/24* | (2006.01) |
| *C07H 3/02* | (2006.01) |
| *A23L 5/41* | (2016.01) |

(52) U.S. Cl.
CPC ............... *C07C 45/85* (2013.01); *A23L 5/41* (2016.08); *C07C 29/143* (2013.01); *C07C 67/42* (2013.01); *C07C 209/24* (2013.01); *C07H 3/02* (2013.01); *A23V 2002/00* (2013.01); *Y02P 20/127* (2015.11)

(58) Field of Classification Search
CPC .......... C07C 45/85; C07C 67/42; C07C 29/14
USPC .................... 568/496, 852; 564/473
See application file for complete search history.

(56) References Cited

U.S. PATENT DOCUMENTS

| | | |
|---|---|---|
| 2,307,937 A | 1/1943 | Marvel |
| 2,494,060 A | 1/1950 | Schofield |
| 2,866,823 A | 12/1958 | Guest et al. |
| 4,200,765 A | 4/1980 | Goetz |
| 4,240,792 A | 12/1980 | Baumgarte et al. |
| 4,317,946 A | 3/1982 | Costa |
| 4,321,414 A | 3/1982 | Costa |
| 4,496,781 A | 1/1985 | Jacobson et al. |
| 5,210,337 A | 5/1993 | Broussard |
| 5,292,541 A | 3/1994 | Underwood et al. |
| 7,094,932 B2 | 8/2006 | Majerski et al. |
| 2012/0271068 A1 | 10/2012 | Mägerlein et al. |

FOREIGN PATENT DOCUMENTS

| | | |
|---|---|---|
| EP | 0 046 680 A1 | 3/1982 |
| JP | H03-246248 A | 11/1991 |
| JP | H08-84592 A | 4/1996 |
| JP | H11-60533 A | 3/1999 |
| WO | WO 02/40436 A1 | 5/2002 |

OTHER PUBLICATIONS

Martin S. Holm et al., "Sn-Beta Catalysed Conversion of Hemicellulosic Sugars", Green Chemistry, vol. 14, No. 3, Jan. 1, 2012, pp. 702-705.

*Primary Examiner* — Sikarl Witherspoon
(74) *Attorney, Agent, or Firm* — Blank Rome LLP

(57) ABSTRACT

A process for reducing the percentage by weight of formaldehyde present in a composition comprising glycolaldehyde, wherein formaldehyde is transformed into one or more formaldehyde acetal(s) and removed from the reactive distillation reaction solution by reactive distillation in the presence of at least one alcohol and a catalyst.

15 Claims, No Drawings

PROCESS FOR REMOVING FORMALDEHYDE FROM A COMPOSITION COMPRISING GLYCOLALDEHYDE

BACKGROUND

The pyrolysis of organic matter such as biomass, wood or sugars, is a known reaction useful for obtaining compositions of bio-oils or low molecular weight carbonyl compounds. The compositions of bio-oils or low molecular weight carbonyl compounds may be referred to as pyrolysis product compositions.

Pyrolysis product compositions, obtained by the pyrolysis of sugars, have been shown to be a useful source of glycolaldehyde. Glycolaldehyde, also known as hydroxyactealdehyde, is the primary low molecular weight carbonyl compound present in the pyrolysis product composition obtained through the pyrolysis of glucose according to U.S. Pat. No. 7,094,932. Additional low molecular weight carbonyl compounds present in the pyrolysis product composition prepared by the pyrolysis of glucose may be: formaldehyde; glyoxal; acetol and pyruvaldehyde.

The pyrolysis product composition of sugars may be used commercially as an aqueous solution in the food industry for use in the browning of foodstuffs, wherein glycolaldehyde is considered to play a significant role as an active ingredient. U.S. Pat. No. 7,094,932 discloses exemplary pyrolysis product compositions obtained by the pyrolysis of sugars suitable for human consumption.

The pyrolysis product composition may be purified to obtain glycolaldehyde. U.S. Pat. No. 5,292,541, discloses an exemplary purification process comprising multiple distillation steps followed by a solvent-induced precipitation to obtain glycolaldehyde. U.S. Pat. No. 7,094,932 discloses the removal of formaldehyde from a pyrolysis product composition by utilizing analytical HPLC.

It is known that pure glycolaldehyde may be used as an intermediate for the preparation of chemicals such as ethylene glycol. U.S. Pat. Nos. 4,200,765, 4,321,414, 4,317,946 and 4,496,781 disclose examples of hydrogenation of pure glycolaldehyde, in particular when pure glycolaldehyde is hydrogenated employing a homogenous ruthenium catalyst.

U.S. Pat. No. 4,496,781 identifies a variety of difficulties encountered when hydrogenating glycolaldehyde in the presence of formaldehyde and indicates that time-consuming separation procedures are required and a reduction in yield of the desired product is observed. U.S. Pat. No. 5,210,337 also highlights that the presence of even a minute amount of formaldehyde, as low as 0.1 wt %, can often poison a hydrogenation catalyst and consequently hinder transformations such as hydrogenation of glycolaldehyde.

In order to overcome the difficulties presented by the presence of formaldehyde in reaction mixtures, extensive investigation of hydrogenation catalysts that are unaffected by the presence of formaldehyde have been undertaken. U.S. Pat. No. 5,210,337 discloses rhenium catalysts resistant to formaldehyde poisoning.

Therefore, there is a need for a process for reducing the weight percentage of formaldehyde present in a pyrolysis product composition comprising low molecular weight carbonyl compounds wherein the process used is high yielding (i.e. a high percentage recovery of the low molecular weight carbonyl compounds), industrially and commercially feasible, and the composition is suitable for use for subsequent chemical transformations.

DISCLOSURE OF THE INVENTION

It has now been discovered that low molecular weight carbonyl compounds, when subjected to specific, catalyzed reactive distillation conditions, are stable. In other words, it is possible to subject a composition comprising low molecular weight carbonyl compounds and formaldehyde to reactive distillation conditions in the presence of an alcohol and catalyst, wherein the formaldehyde will be selectively acetalised and removed from, for example, a pyrolysis product composition comprising low molecular weight carbonyl compounds. It is surprising that glycolaldehyde, a component of the pyrolysis product composition comprising low molecular weight carbonyl compounds, is particularly stable when subjected to reactive distillation conditions. Consequently, the recovery of the glycolaldehyde after the reactive distillation reaction is greater than 80%, greater than 84%, greater than 90% and greater than 95%.

More specifically, the present invention relates to a process for reducing the percentage by weight of formaldehyde present in a composition comprising one or more low molecular weight carbonyl compounds, wherein formaldehyde is transformed into one or more formaldehyde acetal(s) and removed from the reactive distillation reaction solution by reactive distillation in the presence of at least one alcohol and a catalyst.

In a preferred embodiment the composition comprising one or more low molecular weight carbonyl compounds may be an aqueous composition.

In a preferred embodiment the low molecular weight carbonyl compounds comprise compounds selected from the group consisting of glycolaldehyde, glyoxal, pyruvaldehyde and acetol. In a more preferred embodiment, the low molecular weight carbonyl compound is glycolaldehyde.

Formaldehyde acetal relates to the distillate product obtained when formaldehyde is subjected to acid catalyzed reactive distillation conditions in the presence of at least one alcohol. Acetal means compounds in the acetal form and compounds in the hemiacetal form. Formaldehyde acetals formed during the present process may be one or more of the group selected from: formaldehyde dimethylacetal, also known as dimethoxyacetal; formaldehyde ethylmethylacetal, also known as ethoxymethoxymethane; formaldehyde diethylacetal, also known as diethoxymethane and 1,3-dioxolane. In a preferred embodiment the formaldehyde acetal formed during the present process is one or more of formaldehyde dimethylacetal, formaldehyde ethylmethylacetal and formaldehyde diethylacetal. More preferably the formaldehyde acetal formed during the present process is formaldehyde dimethylacetal.

In a preferred embodiment one or more alcohols may be selected from any low molecular weight alcohols that may form an acetal with formaldehyde. Preferably the alcohol is selected from one or more of the group consisting of methanol, ethanol, ethylene glycol and propylene glycol. In a preferred embodiment the alcohol or alcohols present in the reactive distillation reaction solution are present in a volume by weight percent of between 10% and 90%. In a further preferred embodiment the alcohol or alcohols present in a volume by weight percent of between 30% and 70%. The volume of alcohol in the reactive distillation reaction solution may also be expressed as a ratio of volume of alcohol or alcohols to volume of aqueous composition comprising one or more low molecular weight carbonyl compounds. Ratios include between 1:9 and 9:1 or greater than 1:9 of the volume of alcohol or alcohols to volume of aqueous composition comprising one or more low molecular weight carbonyl compounds. Preferred ratios include ratios of 1:1 or greater such as: 1:1, 2:1, 3:1, 4:1, 5:1 and 9:1 of the volume of alcohol or alcohols to volume of aqueous composition comprising one or more low molecular weight carbonyl compounds.

In an alternative preferred embodiment the composition comprising one or more low molecular weight carbonyl compounds may be present in a reactive distillation reaction solution comprising methanol only as the solvent.

The volume by weight percent of an aqueous composition comprising one or more low molecular weight carbonyl compounds in the reactive distillation reaction solution may be from between 10% to 90% or from between 30% to 70%.

Reactive distillation reaction solution means the combination of a pyrolysis product composition comprising low molecular weight carbonyl compounds, at least one alcohol, one or more solvents and one or more catalyst.

Solvent means one or more liquids selected from the group consisting of one or more alcohols, water or an organic solvent. The proper use and understanding of the term organic solvent is self-explanatory and lies well within the ability of the person skilled in the art of reactive distillation.

The solvent and the alcohol may be the same liquid, e.g. methanol.

Catalyst relates to any catalyst that enables the pH of the reactive distillation reaction solution to preferably be below 7, i.e. an acid catalyst, or a solid catalyst able to catalyse the reactive distillation reaction. The catalyst may be a homogenous or heterogeneous catalyst. The catalyst may be an acid catalyst for example, a solid acid catalyst, a mineral acid, Brønsted acid and/or an organic acid. The catalyst may be in the form of an ion exchange resin (acid resin), or molecular sieves. Even more preferably the acid catalyst is selected from the group consisting of Amberlyst-131 and concentrated sulphuric acid.

An alternative acid catalyst for use in reactive distillation reactions may be $FeCl_3$. J Mol. Cat. A (2003) 202, pp 41-46 describes acetalization of carbonyl groups in the presence an alcohol or diol and $FeCl_3$.

Reactive distillation relates to reaction conditions that facilitate the formation and removal of formaldehyde acetal(s) from the reaction solution during the present process. In relation to the present invention, the process of reactive distillation encompasses two functions:
  a) The formation of one or more formaldehyde acetal(s) by heating the reactive distillation reaction solution, i.e. heating formaldehyde in the presence of one or more alcohols and a catalyst; and
  b) The removal of one or more formaldehyde acetal(s) from the reactive distillation reaction solution by distillation.

Reactive distillation conditions relate to the temperature, pressure, solvent and pH of reaction solution and duration of the process of the present invention. The process may be performed at a temperature of up to 120° C., between 64 and 110° C., between 70 and 100° C., between 70 and 95° C., between 70 and 90° C. In a preferred embodiment the reactive distillation reaction is carried out under atmospheric or reduced pressure. Reduced pressure means between 100 mBar and atmospheric pressure. In a preferred embodiment the process of the present invention is performed at atmospheric pressure, at a temperature of up to 120° C., in a reactive distillation reaction solution comprising one or more low molecular weight carbonyl compounds, one or more alcohols, water, and a catalyst for up to 24 hours. More preferably, the process is performed at atmospheric pressure, between 64 and 110° C., in a reactive distillation reaction solution comprising one or more low molecular weight carbonyl compounds, methanol, water and a catalyst, for up to 7 hours. Even more preferably the process is performed at atmospheric pressure, between 70 and 100° C., in a reactive distillation reaction solution comprising glycolaldehyde, methanol, water and an acid catalyst, for between 5 and 7 hours. A composition comprising low molecular weight carbonyl compounds relates to the product composition or mixture obtained by the pyrolysis of organic matter such as wood or biomass, or a sugar. In a preferred embodiment the composition comprising low molecular weight carbonyl compounds is obtained by pyrolysis of one or more sugars selected from the groups consisting of glucose, sucrose, xylose, fructose and galactose. Alternatively, a composition comprising one or more low molecular weight carbonyl compounds, for example glycolaldehyde, may relate to product composition obtained by a hydroformylation reaction of carbon monoxide, formaldehyde and hydrogen, as described in U.S. Pat. No. 4,496,781.

The composition comprising one or more low molecular weight carbonyl compounds obtained from the process of the present invention, i.e. after the composition has been subjected to reactive distillation conditions of the present invention, is a composition free, or substantially free, from formaldehyde. This composition is called a reactive distillation product solution. For example, the composition comprises less than 1.5 percent by weight of formaldehyde. For example, the composition comprises less than 1.0 percent by weight of formaldehyde. Preferably the composition comprises less than 0.5 percent by weight of formaldehyde. More preferably the composition comprises less than 0.1 percent by weight of formaldehyde. Even more preferably the composition comprises less than 0.05 percent by weight of formaldehyde. Even more preferably the composition comprises a percentage by weight of formaldehyde that does not prevent further transformations of the low molecular weight carbonyl compounds.

The low molecular weight carbonyl compounds of the reactive distillation product solution obtained from the process of the present invention may be difficult to hydrogenate since the low molecular weight carbonyl compounds may be present partly as dimethyl acetals or hemiacetals. The reactive distillation product solution comprising low molecular weight carbonyl compounds in their carbonyl, rather than corresponding acetal form, can be obtained by removing or reducing the volume of the alcohol present in reactive distillation product solution in the presence of a catalyst, preferably an acid catalyst. Optionally, a solvent such as water may be added to the solution and the solution may be heated. Heating the reaction solution reduces the volume of the solution, preferably reducing or removing the volume of alcohol comprised in the reaction solution.

The reduction in weight percent of formaldehyde present in the composition comprising one or more low molecular weight carbonyl compounds obtained by the process of the present invention (the reactive distillation product) enables the low molecular weight carbonyl compounds to be subjected to reaction conditions that have not been possible previously due to the presence of formaldehyde. Therefore, subsequent transformations of the low molecular weight carbonyl compounds present in the reactive distillation product are possible.

It is desirable to lower the percentage by weight of formaldehyde present in a composition comprising one or more low molecular weight carbonyl compounds in order to enable subsequent transformations of the low molecular weight carbonyl compounds that are typically hindered by the presence of formaldehyde, for example, hydrogenation of glycolaldehyde or glyoxal to ethylene glycol, or hydrogenation of pyruvaldehyde or acetol to propylene glycol as disclosed in EP 2 298 722 A2 and US 2008/0242898. Such hydrogenation reactions may be performed in the presence of a metal catalyst, for example copper, nickel, molybdenum, cobalt, iron, chromium, zinc, and the platinum group metals. In a preferred embodiment the metal catalyst is selected from the group consisting of palladium or ruthenium on carbon or nickel and the hydrogenation reaction is performed according to the experimental methods disclosed in U.S. Pat. Nos. 4,200,765, 4,321,414, 4,317,946, 4,496,781 and 5,210,337.

The proper use and understanding of the term metal catalyst is self-explanatory and lies well within the ability of the person skilled in the art of hydrogenation. Examples of further suitable metal catalysts for use in hydrogenation reactions are disclosed in Ullmann's Encyclopaedia of Industrial Chemistry: Hydrogenation and Dehydrogenation.

The reactive distillation product obtained from the process of the present invention may be used as a component for the preparation of flexible phenolic carbamido resins. U.S. Pat. No. 3,763,272 provides examples of preparation methods of flexible phenolic carbamido resins comprising the use of compounds comprising a carbonyl functional group. Similarly, WO 2009/040415 and WO 2013/0150123 provide examples of compounds comprising a carbonyl functional group for use in the preparation of water dilutable resin compositions and binders. These resins and binders may be used, for example, in the production of fibres, textiles, plastics, rubbers, plywood and mineral wool.

The reactive distillation product obtained from the process of the present invention may be used to prepare straight and branched chain oxygenated $C_4$-alkyl and $C_4$-alkenyl compounds such as one or more of the group consisting of methyl vinylglycolate (methyl 2-hydroxy-3-butenoate), methyl lactate, erythrose and threose, or their corresponding polyols (erythritol and threitol) as described in Holm et al. Green Chemistry (2012) 12, p 702; Lambert et al. Science (2010) 327, p 98; Weber et al. PNAS (2006) 103, 34, pp 12713-12717; Org. Biomol. Chem. (2005) 3, pp 1850-1855; and Kinetics and Catalysis (2009) 50, 2, pp 297-303. Exemplary reactions are described in Holm et al. Green Chemistry (2012) 12, p 702.

The reactive distillation product may be subjected to reductive amination reaction conditions in order to prepare amines such as ethanolamine, ethylenediamine, dimethylethanolamine or dimethylethanolamine as described in US2012/0271068. As the reactive distillation product comprises a reduced percent by weight of formaldehyde, it is possible for the reduction (hydrogenation) step of this transformation to be carried out under conditions such as those described according to the experimental methods disclosed in U.S. Pat. No. 4,200,765, 4,321,414, 4,317,946, 4,496,781 and 5,210,337. Additionally, it is possible for this transformation to become a one-step, rather than two-step process, as described in US 2012/0271068. Exemplary reaction conditions are described in US 2012/0271068. Exemplary aminating agents would include: primary or secondary aliphatic amines, or ammonia; wherein the aliphatic substituent may be a carbon chain of one to four carbon atoms selected from one or more of: straight or branched chain methyl, ethyl, propyl and butyl alkyl carbon chains as described in US2012/0271068. Examples of aliphatic amines are: monomethylamine and dimethylamine.

A further use of the reactive distillation product is for browning of foodstuffs as described in U.S. Pat. No. 7,094,932.

Preparation of a composition comprising one or more low molecular weight carbonyl compounds:

EXAMPLE 1

A composition comprising one or more low molecular weight carbonyl compounds was obtained by pyrolysis of a 10 wt. % aqueous glucose (D-glucose monohydrate; Sigma Aldrich) solution as described in U.S. Pat. No. 7,094,932. The typical composition of the pyrolysis product composition is given in Table 1.

TABLE 1

|  | GLA (g/l) | GLO (g/l) | PYR (g/l) | FOR (g/l) | ACE (g/l) |
|---|---|---|---|---|---|
| Example 1 | 67.0 | 3.5 | 8.2 | 6.8 | 1.3 |

GLA = Glycolaldehyde
GLO = Glyoxal
PYR = Pyruvaldehyde
FOR = Formaldehyde
ACE = Acetol Removing Formaldehyde from a composition comprising One or more low molecular weight carbonyl compounds:

EXAMPLE 2

300 ml methanol along with 10 g of the Brønsted acidic resin Amberlyst-131 (Sigma Aldrich) was added to 300 ml of an aqueous solution of the pyrolysis product composition comprising one or more low molecular weight carbonyl compounds obtained in Example 1. The solution was transferred to a reactive distillation setup. An inert atmosphere was established by passing 20 ml/min of $N_2$ through the reaction solution while stirring before heating the solution until boiling at approximately between 78 to 79° C. Small amounts of distillate product were continuously condensed from the top of the distillation column and collected. A constant volumetric ratio of methanol and aqueous solution (and constant temperature of the boiling solution) was achieved by continuously adding a volume of methanol equivalent to the volume recovered as distillate product. The distillate product was analyzed by gas chromatography and shown to contain mainly methanol and formaldehyde dimethyl acetal formed by acetalization of formaldehyde in the solution. Small amounts of methyl formate, methyl acetate, acetaldehyde and acetaldehyde dimethyl acetal were also detected.

After 5-7 hours of reaction time the remaining reactive distillation reaction solution was analyzed by HPLC and less than 0.01% by weight of formaldehyde was detected. The HPLC analysis was performed on an Aminex HPX-87H column with a 0.005 M $H_2SO_4$ eluent which converted all acetals into the aldehydes before detection.

EXAMPLE 3

A reactive distillation reaction as described in Example 2 was performed with the exception that 150 ml methanol was added to 450 ml of an aqueous solution of the composition comprising one or more low molecular weight carbonyl compounds obtained in Example 1. The boiling point of the reactive distillation reaction solution was approximately between 85 and 86° C.

EXAMPLE 4

A reactive distillation as described in Example 2 was performed with the exception that 450 ml methanol was added to 150 ml of an aqueous solution of the composition comprising one or more low molecular weight carbonyl compounds obtained in Example 1. The boiling point of the reaction solution was approximately 72° C.

EXAMPLE 5

A reactive distillation reaction as described in Example 2 was performed with the exception that 2 g of concentrated sulfuric acid was used as the acetalization catalyst instead of the 10 g Amberlyst-131 used in Example 1.

EXAMPLE 6

A reactive distillation reaction as described in Example 2 was performed with the exception that 300 ml ethanol instead of 300 ml methanol was used and the reaction time was increased to approximately 10 hours. The distillate contained mainly ethanol and formaldehyde diethyl acetal.

EXAMPLE 7

A reactive distillation reaction as described in Example 2 was performed with the exception that 300 ml ethyleneglycol instead of 300 ml methanol was used. The boiling point of the reactive distillation reaction solution was approximately between 107-108° C. The distillate product contained mainly water and 1,3-dioxolane.

Table 2 shows the content of the major components in the reactive distillation reaction solution before and after the reactive distillation reaction of the present invention.

TABLE 2

| Example | | Glycolaldehyde (g) | Glyoxal (g) | Pyruvaldehyde (g) | Formaldehyde (g) | Acetol (g) |
|---|---|---|---|---|---|---|
| 2 | B | 19.9 | 1.1 | 2.5 | 2.1 | 0.5 |
|   | A | 19.1 | 1.0 | 2.1 | 0.0 | 0.4 |
| 3 | B | 30.2 | 1.6 | 3.7 | 3.1 | 0.6 |
|   | A | 25.5 | 1.9 | 2.6 | 0.0 | 0.6 |
| 4 | B | 8.7 | 0.6 | 1.4 | 1.3 | 0.3 |
|   | A | 8.5 | 0.5 | 1.2 | 0.0 | 0.3 |
| 5 | B | 16.6 | 1.1 | 2.5 | 2.4 | 0.6 |
|   | A | 16.4 | 0.9 | 2.2 | 0.0 | 0.6 |
| 6 | B | 17.0 | 1.1 | 2.6 | 2.6 | 0.6 |
|   | A | 13.7 | 1.3 | 1.8 | 0.0 | 0.8 |

B means the composition before the composition comprising one or more low molecular weight carbonyl compounds is subjected to the conditions of the present invention, i.e. reactive distillation.
A means the composition after the composition comprising one or more low molecular weight carbonyl compounds is subjected to the conditions of the present invention, i.e. reactive distillation.

Table 3 shows the percentage by weight of formaldehyde removal and the percentage weight recovery of glycolaldehyde and pyruvaldehyde compared to the composition of Example 1, Table 1 (the pyrolysis product composition), i.e. the composition comprising one or more low molecular weight carbonyl compounds before it is subjected to the conditions of the present invention.

TABLE 3

| Example | Removal of formaldehyde | Recovery of glycolaldehyde | Recovery of pyruvaldehyde |
|---|---|---|---|
| 2 | >99% | 96% | 84% |
| 3 | >99% | 84% | 70% |
| 4 | >99% | 98% | 86% |
| 5 | >99% | 99% | 88% |
| 6 | >99% | 81% | 69% |

Recovery of the free aldehyde of the low molecular weight carbonyl compounds.

EXAMPLE 7

GC and HPLC analysis of the reactive distillation product solution from Example 2, from here on named solution A, revealed that 53% of the glycolaldehyde in the solution was present as glycolaldehyde dimethyl acetal.

0.5 g Amberlyst-131 was added to 100 ml of solution A and placed in a rotary evaporator. After 4 hours at reduced pressure (about 100 mbar) and 50° C., all methanol and approximately half the water had been evaporated. Amberlyst-131 was removed from the solution by filtration and GC and HPLC analysis of the concentrated solution revealed that it contained no glycolaldehyde dimethyl acetal.

Table 4 shows the amount of remaining methanol, the content of glycolaldehyde dimethyl acetal in the concentrated solution and the amount of recovered glycolaldehyde and pyruvaldehyde compared to solution A.

TABLE 4

| Example | Removal of methanol | Recovery of glycolaldehyde | Recovery of pyruvaldehyde | Glycoladehyde present as glycolaldehyde dimethyl acetal |
|---|---|---|---|---|
| 7 | >99% | >95% | 87% | <0.5% |

Hydrogenation of low molecular weight carbonyl compounds.

EXAMPLE 8

0.50 g crystalline glycolaldehyde dimer (Sigma Aldrich) was dissolved in 15 ml of water and loaded in an autoclave (50 ccm) along with 0.10 g of the hydrogenation catalyst 5% Ru supported on carbon. The autoclave was purged 3 times with hydrogen and subsequently pressurized to 30 bars with $H_2$. The solution was heated to 60° C. from room temperature in the course of 15 min and kept at this temperature for 3 hours while stirred. After reaction the autoclave was cooled to room temperature and the decrease in $H_2$ pressure was noted.

The product mixture was isolated from the catalyst by filtration and analyzed by HPLC and GC.

The yield of ethylene glycol was >98%.

TABLE 5

Yields of ethylene glycol from example 8-17.

| | Yield of ethyleneglycol (carbon %) |
|---|---|
| Example 8 | >98% |
| Example 9 | 42.8% |

TABLE 5-continued

Yields of ethylene glycol from example 8-17.

| | Yield of ethyleneglycol (carbon %) |
|---|---|
| Example 10 | 40.0% |
| Example 11 | 66.8% |
| Example 12 | 95.4% |
| Example 13 | 97.3% |

EXAMPLE 9

0.50 g crystalline glycolaldehyde dimer (Sigma Aldrich) was dissolved in 15 ml of water and hydrogenated as described in Example 8 with the exception that 0.056 g of formaldehyde was added to the glycolaldehyde solution before the catalyst was added.

The yield of ethylene glycol was 42.8%.

EXAMPLE 10

7.5 g of the composition comprising one or more carbonyl compounds obtained in Example 1 and as described in Table 1 (containing 0.50 g glycolaldehyde) was added to 8.0 g water and loaded in an autoclave along with 0.10 g of the hydrogenation catalyst 5% Ru on Carbon. The autoclave was purged 3 times with hydrogen and subsequently pressurized to 30 bars with $H_2$. The mixture was heated to 60° C. from room temperature in the course of 15 min and kept at this temperature for 3 hours while stirred. After reaction the autoclave was cooled to room temperature and the decrease in $H_2$ pressure was noted.

The hydrogenated product mixture was isolated from the catalyst by filtration and analyzed by HPLC.

The maximum theoretical yield of ethylene glycol was based on hydrogenation of both glyoxal and glycolaldehyde into ethylene glycol.

The yield of ethylene glycol was 40.0%.

EXAMPLE 11

1.9 g of water was added to 13.7 g of solution A prepared in Example 2 giving a solution which contained 0.5 g of glycolaldehyde and the solution was hydrogenated as described in Example 8.

The maximum theoretical yield of ethylene glycol was based on hydrogenation of both glyoxal and glycolaldehyde into ethylene glycol.

The yield of ethylene glycol was 66.8%.

EXAMPLE 12

1.9 g water was added to 13.7 g of solution A prepared in Example 2 containing 0.50 g of glycolaldehyde and the solution was hydrogenated as described in Example 8 with exception that the addition that 0.2 g of Amberlyst-131 was added to the solution along with the hydrogenation catalyst.

The maximum theoretical yield of ethylene glycol was based on hydrogenation of both glyoxal and glycolaldehyde into ethylene glycol.

The yield of ethylene glycol was 95.4%.

EXAMPLE 13

12.3 g of water was added to 3.2 g of the concentrated product obtained in Example 7 containing 0.50 g of glycolaldehyde. The solution was hydrogenated as described in Example 8.

The maximum theoretical yield of ethylene glycol was based on hydrogenation of both glyoxal and glycolaldehyde into ethylene glycol.

The yield of ethylene glycol was 97.3%.

The invention claimed is:

1. A process for reducing the percentage by weight of formaldehyde present in a composition, comprising:
   a) mixing an aqueous feed composition comprising glycoaldehyde at a first concentration and formaldehyde with an alcohol in a volume ratio of 1:9 to 9:1 to obtain a reactive distillation reaction solution;
   b) contacting the reactive distillation reaction solution with an acid catalyst while distilling formaldehyde acetal produced in the reactive distillation to obtain a reactive distillation product solution; and
   c) contacting the reactive distillation product solution with an acid catalyst while distilling excess alcohol from the reactive distillation product solution to obtain a final product solution comprising aqueous glycolaldehyde having a concentration greater than said first concentration.

2. A process according to claim 1, wherein the alcohol is selected from one or more of the group consisting of methanol, ethanol, ethylene glycol and propylene glycol.

3. A process according to claim 1, wherein the acid catalyst is selected from one or more of the group consisting of a solid catalyst, mineral acid catalyst and organic acid.

4. A process according to claim 1, wherein the acid catalyst is selected from one or more of the group consisting of an acidic resin, molecular sieves and a mineral acid.

5. A process according to claim 1, wherein the acid catalyst is selected from one or more of the group consisting of Brønsted acidic resins and concentrated sulphuric acid.

6. A process according to claim 1, wherein the distillation is carried out at a temperature less than 120° C.

7. A process according to claim 1, wherein the distillation is carried out under reduced pressure.

8. A process according to claim 1, further comprising adding water to the reaction solution after reactive distillation, heating and reducing the volume of the solution.

9. A process according to claim 1, wherein the feed composition comprising glycolaldehyde is obtained by pyrolysis of organic matter selected from the group consisting of biomass, wood and sugars.

10. A process according to claim 1, wherein the feed composition comprising glycolaldehyde is obtained by pyrolysis of one or more sugars selected from the group consisting of glucose, sucrose, xylose, fructose and galactose.

11. A process according to claim 1, wherein the feed composition comprising glycolaldehyde is obtained by hydroformylation.

12. A process for the preparation of ethylene glycol, comprising subjecting the final product solution prepared according to claim 1 to hydrogenation.

13. A process for the preparation of amines wherein the product solution composition comprising glycolaldehyde according to claim 1 is reductively aminated.

14. A process for preparing straight and branched chain oxygenated C4-alkyl and C4-alkenyl compounds, comprising: providing the final product solution according to claim 1, and converting the glycolaldehyde to straight and branched chain oxygenated C4-alkyl and C4-alkenyl compounds.

15. A process for reducing the formaldehyde content of a glycolaldehyde composition, comprising:

a) mixing an aqueous feed composition comprising at least 8.5 wt. % glycolaldehyde with an alcohol in a volume ratio of 1:9 to 9:1 to obtain a reactive distillation reaction solution;
b) contacting the reactive distillation reaction solution with an acid catalyst while distilling formaldehyde acetal produced in the reactive distillation to obtain a reactive distillation product solution; and
c) contacting the reactive distillation product solution with an acid catalyst while distilling excess alcohol from the reactive distillation product solution to obtain a final product solution comprising glycolaldehyde having a concentration greater than that of said aqueous feed.

\* \* \* \* \*